(12) United States Patent
Winslow et al.

(10) Patent No.: US 8,998,994 B2
(45) Date of Patent: Apr. 7, 2015

(54) HUMERAL IMPLANT HAVING A FLOATING BEARING

(71) Applicant: Biomet Manufacturing Corp., Warsaw, IN (US)

(72) Inventors: Nathan A. Winslow, Warsaw, IN (US); John M. McDaniel, Warsaw, IN (US)

(73) Assignee: Biomet Manufacturing, LLC, Warsaw, IN (US)

( * ) Notice: Subject to any disclaimer, the term of this patent is extended or adjusted under 35 U.S.C. 154(b) by 0 days.

(21) Appl. No.: 13/744,535

(22) Filed: Jan. 18, 2013

(65) Prior Publication Data

US 2013/0204375 A1 Aug. 8, 2013

Related U.S. Application Data

(60) Provisional application No. 61/595,852, filed on Feb. 7, 2012.

(51) Int. Cl.
*A61F 2/40* (2006.01)
*A61F 2/30* (2006.01)
*A61B 17/84* (2006.01)

(52) U.S. Cl.
CPC ............... *A61F 2/40* (2013.01); *A61F 2/4014* (2013.01); *A61F 2/4081* (2013.01); *A61F 2002/30331* (2013.01); *A61F 2002/30332* (2013.01); *A61F 2002/30387* (2013.01); *A61F 2002/30518* (2013.01); *A61F 2002/30594* (2013.01); *A61F 2002/30649* (2013.01); *A61F 2002/30662* (2013.01); *A61F 2002/30884* (2013.01); *A61F 2002/4022* (2013.01); *A61F 2002/4085* (2013.01); *A61B 17/842* (2013.01); *A61F 2002/30064* (2013.01); *A61F 2002/30398* (2013.01); *A61F 2002/30604* (2013.01)

(58) Field of Classification Search
CPC ............ A61F 2/40; A61F 2/4081; A61F 2/38
USPC .......... 623/19.11–20.13, 20.32–20.33, 22.11, 623/22.15–22.19
See application file for complete search history.

(56) References Cited

U.S. PATENT DOCUMENTS

| | | | |
|---|---|---|---|
| 3,916,451 | A | 11/1975 | Buechel et al. |
| 6,228,119 | B1 | 5/2001 | Ondrla et al. |
| 6,514,287 | B2 | 2/2003 | Ondrla et al. |

(Continued)

FOREIGN PATENT DOCUMENTS

| | | |
|---|---|---|
| DE | 19548154 A1 | 6/1997 |
| FR | 2821545 A1 | 9/2002 |
| FR | 2955248 A1 | 7/2011 |

OTHER PUBLICATIONS

Written Opinion (B130016 B-1169-PCT).Mar. 22, 2013.

*Primary Examiner* — Yashita Sharma
(74) *Attorney, Agent, or Firm* — Harness, Dickey

(57) ABSTRACT

A shoulder can include a fixed bearing having a generally spherical articulating surface configured to be coupled to a glenoid. The implant can also include a floating bearing member defining a first spherical bearing surface and a second planar articulating bearing surface. The implant can include a stem defining a stem planar bearing surface coupled to the second planar articulating bearing surface. The second planar articulating bearing surface can cooperate with the stem planar bearing surface to enable the floating bearing to translate relative to the stem.

13 Claims, 9 Drawing Sheets

(56) References Cited

U.S. PATENT DOCUMENTS

| | | |
|---|---|---|
| 6,599,321 B2 | 7/2003 | Hyde, Jr. |
| 7,033,396 B2 | 4/2006 | Tornier |
| 7,465,319 B2 | 12/2008 | Tornier |
| 7,470,287 B2 | 12/2008 | Tornier et al. |
| 2006/0020344 A1* | 1/2006 | Shultz et al. ............ 623/19.12 |
| 2008/0288079 A1* | 11/2008 | Leibel .................... 623/20.11 |
| 2012/0004733 A1 | 1/2012 | Hodorek et al. |
| 2012/0191201 A1* | 7/2012 | Smits et al. ............ 623/19.11 |

\* cited by examiner

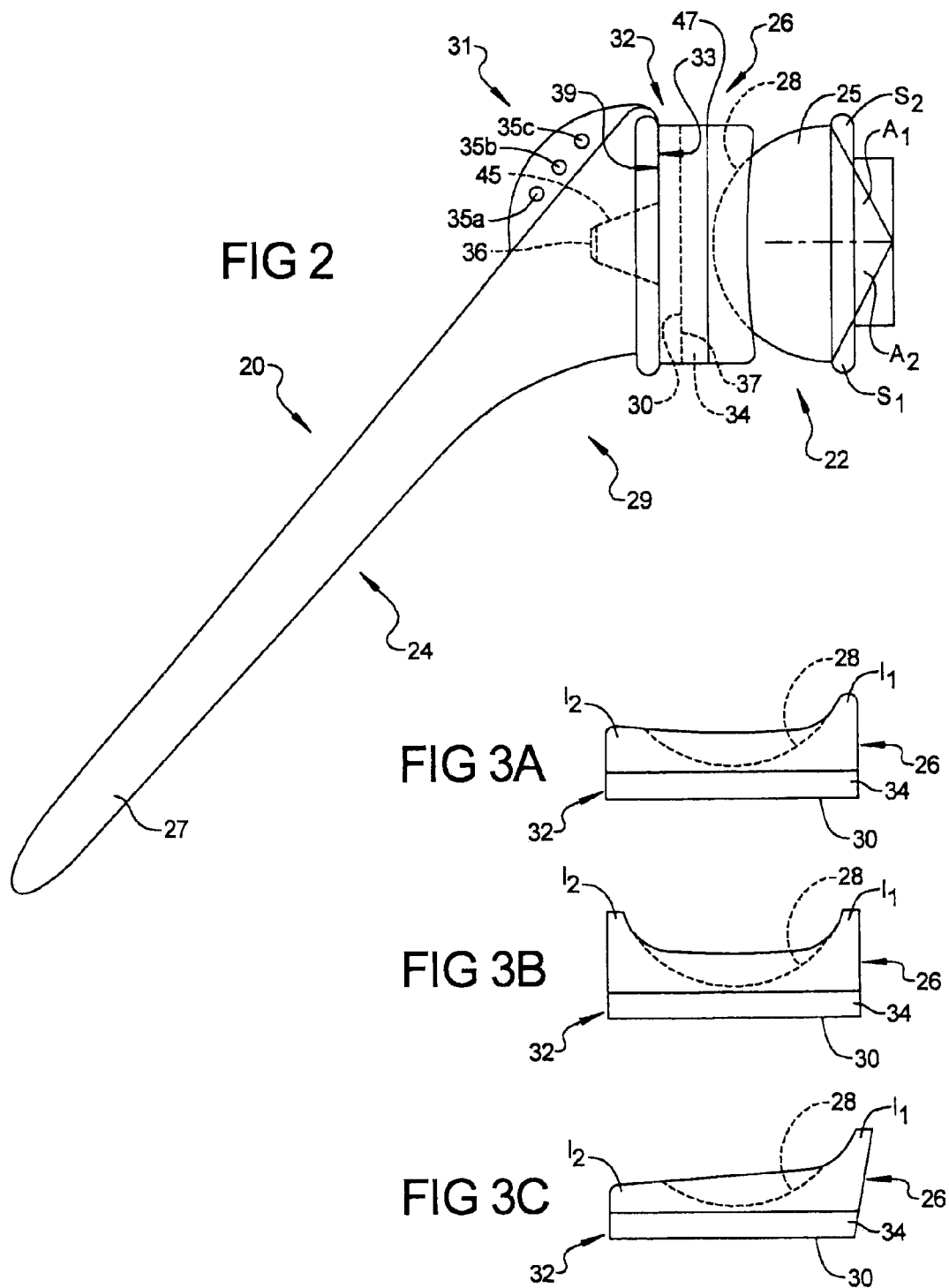

HUMERAL IMPLANT HAVING A FLOATING BEARING

CROSS-REFERENCE TO RELATED APPLICATIONS

This application claims the benefit of U.S. Provisional Application No. 61/595,852, filed on Feb. 7, 2012. The entire disclosure of the above application is incorporated herein by reference.

INTRODUCTION

It is not uncommon for the exterior surface of the humeral head to become damaged or defective over time. Conventionally, a variety of humeral head resurfacing implants exist for repairing humeral head surfaces. While conventional humeral head resurfacing implants are suitable for their intended uses, such implants are subject to improvement.

Motion of a natural shoulder is kinematically complex. During a relatively broad range of flexion and extension, the articular or bearing surfaces of a natural shoulder experience rotation, medial and lateral angulation, translation, rollback and sliding. Shoulder joint implants, in combination with ligaments and muscles, attempt to duplicate this natural shoulder motion, as well as absorb and control forces generated during the range of motion. Depending on the degree of damage or deterioration of the shoulder tendons and ligaments, however, it may be necessary for a shoulder joint implant to limit one or more of these motions in order to provide adequate stability.

The present disclosure relates to a humeral implant for total shoulder joint replacement and more specifically relates to a humeral implant having a floating bearing.

SUMMARY

This section provides a general summary of the disclosure, and is not a comprehensive disclosure of its full scope or all of its features.

Various aspects of the teachings provide a modular humeral implant, associated kit and method for implantation into a humerus that includes a natural humeral shaft and a natural humeral head. The modular implant includes a humeral stem for implantation into the natural humeral shaft, a floating bearing coupled to the stem, and a fixed articulating bearing coupled to the glenoid. The fixed bearing includes an exterior hemispherical articulating surface defining a terminating rim and stop, an interior surface opposite to the exterior articulating surface, and a first coupling mechanism for coupling the articulating bearing to the glenoid. The anchoring stem is coupled to the interior surface and extends along a stem axis that extends through an axial center of the head. The stop protrudes from only a portion of the head when fastened thereto and is operable to engage with the floating bearing. The floating bearing includes a second coupling mechanism configured to cooperate with the stem to allow linear translation of the floating bearing with respect to the stem. The floating bearing further has an outer articulating surface that is curved along substantially its entire length and is substantially flush with the exterior hemispherical articulating surface when the stop is engaged with the floating bearing.

The present teachings also provide for a humeral head implant including a floating bearing, an anchoring stem, and a head having a convex articulating surface fixably coupled to the glenoid. The head includes an exterior hemispherical articulating surface defining a terminating rim. The terminating rim defines a stop extending from a first side of the terminating rim to a second side of the terminating rim. The head also includes an interior coupling surface opposite to the exterior articulating surface and a first coupling mechanism proximate to the stop. A fastening member can be coupled to the coupling surface and extends along a stem axis that extends through an axial center of the head and through the stop plane. The stem axis can be perpendicular to the stop plane. The stop protrudes from a portion of the head and extends across the plane when fastened to the head.

The present teachings also provide for a method of resurfacing a humeral head of an implant site. The method can include resecting the humeral head so as to form a generally planar surface and coupling a stem to the resected humerus. The method can include selecting a floating bearing having a first coupling mechanism from a plurality of floating bearings of different sizes and attaching the first coupling mechanism of the floating bearing to the stem. The method can also include coupling a hemispherical bearing member to a prepared glenoid and coupling the floating bearing to the hemispherical bearing.

In another aspect, the present teachings provide a modular humeral implant for implantation into a humerus that includes a natural humeral shaft and a natural humeral head. The implant includes a humeral stem implantable into the natural humeral shaft, and a linear floating bearing couplable to the humeral stem, the linear floating bearing coupled to a fixed bearing positioned on a prepared glenoid.

In another aspect, the implant includes a humeral stem for implantation into the natural humeral shaft, and a floating bearing support plate in the form of a substantially planar plate including a coupling mechanism, the planar plate coupled to the humeral stem with a taper lock connection and adapted for slidable engagement with the floating bearing.

In yet another aspect, the implant includes a humeral stem for implantation into the natural humeral shaft, and a floating bearing in the form of a substantially planar floating bearing including a substantially spherical bearing surface. The floating bearing includes a tapered projection received in a tapered recess of the humeral stem which allows linear translation, and the floating bearing can be adapted for coupling to a spherical bearing coupled to a prepared glenoid.

Further areas of applicability will become apparent from the description provided herein. The description and specific examples in this summary are intended for purposes of illustration only and are not intended to limit the scope of the present disclosure.

BRIEF DESCRIPTION OF THE DRAWINGS

The drawings described herein are for illustrative purposes only of selected embodiments and not all possible implementations, and are not intended to limit the scope of the present disclosure.

FIG. 2 is an assembled view of a humeral implant according to the present teachings;

FIGS. 3A-3C are optional floating bearings according to the present teachings;

DETAILED DESCRIPTION

Figure 1:
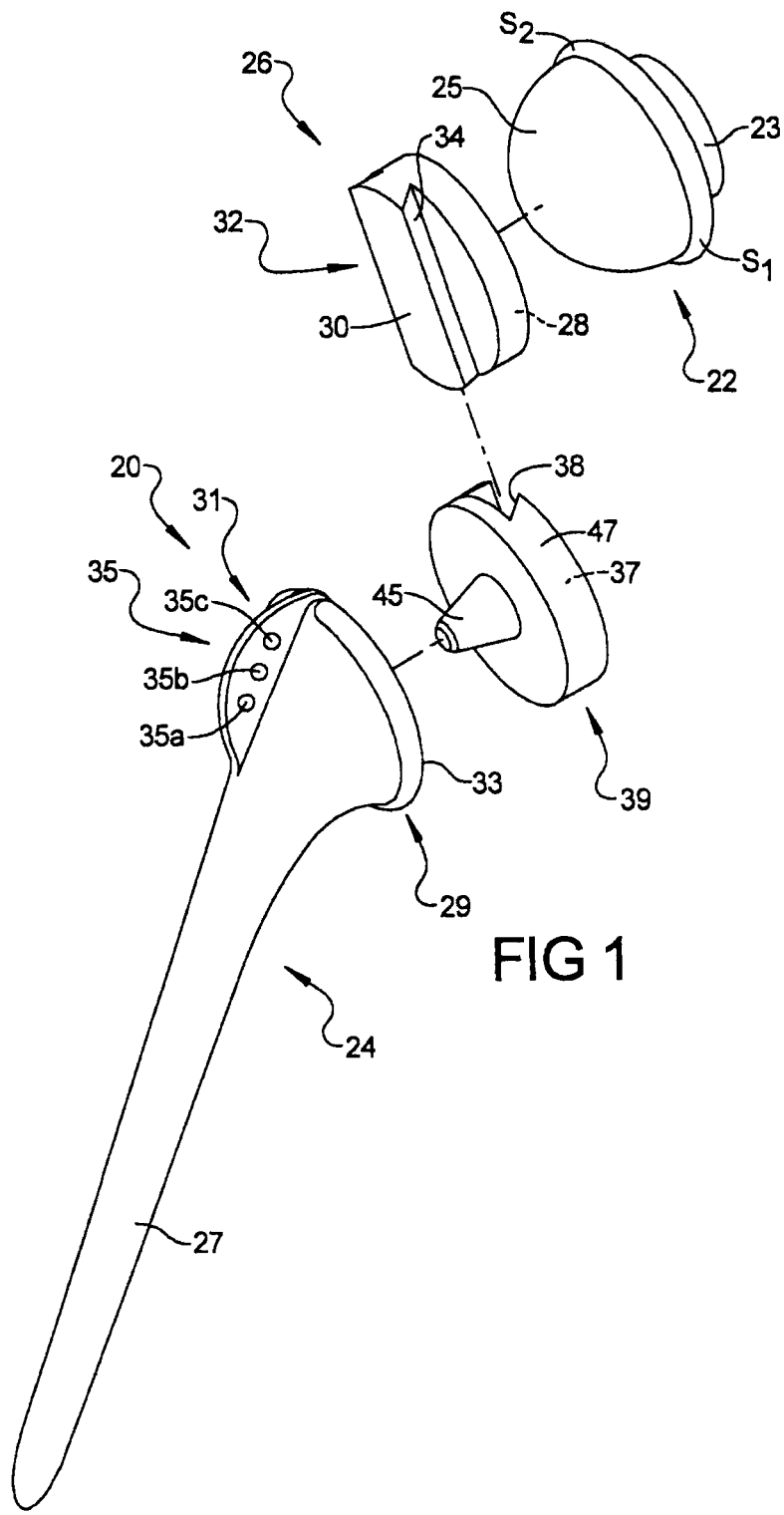
FIG. 1 is an exploded view of a humeral implant according to the present teachings.

The following description is merely exemplary in nature and is not intended to limit the present teachings, application, or uses. It should be understood that throughout the drawings, corresponding reference numerals indicate like or corresponding parts and features. Although the following description is related generally to a humeral implant having a floating bearing for use in an anatomy to restore function to damaged tissue, such as in the case of shoulder joint, it will be understood that the teachings of the implant system as described and claimed herein can be used in any appropriate surgical procedure. For example, the teachings of the implant system described and claimed herein can be applied to repair any suitable anatomical joint, such as hip joint. Therefore, it will be understood that the following discussions are not intended to limit the scope of the present teachings and claims herein.

Figure 11:
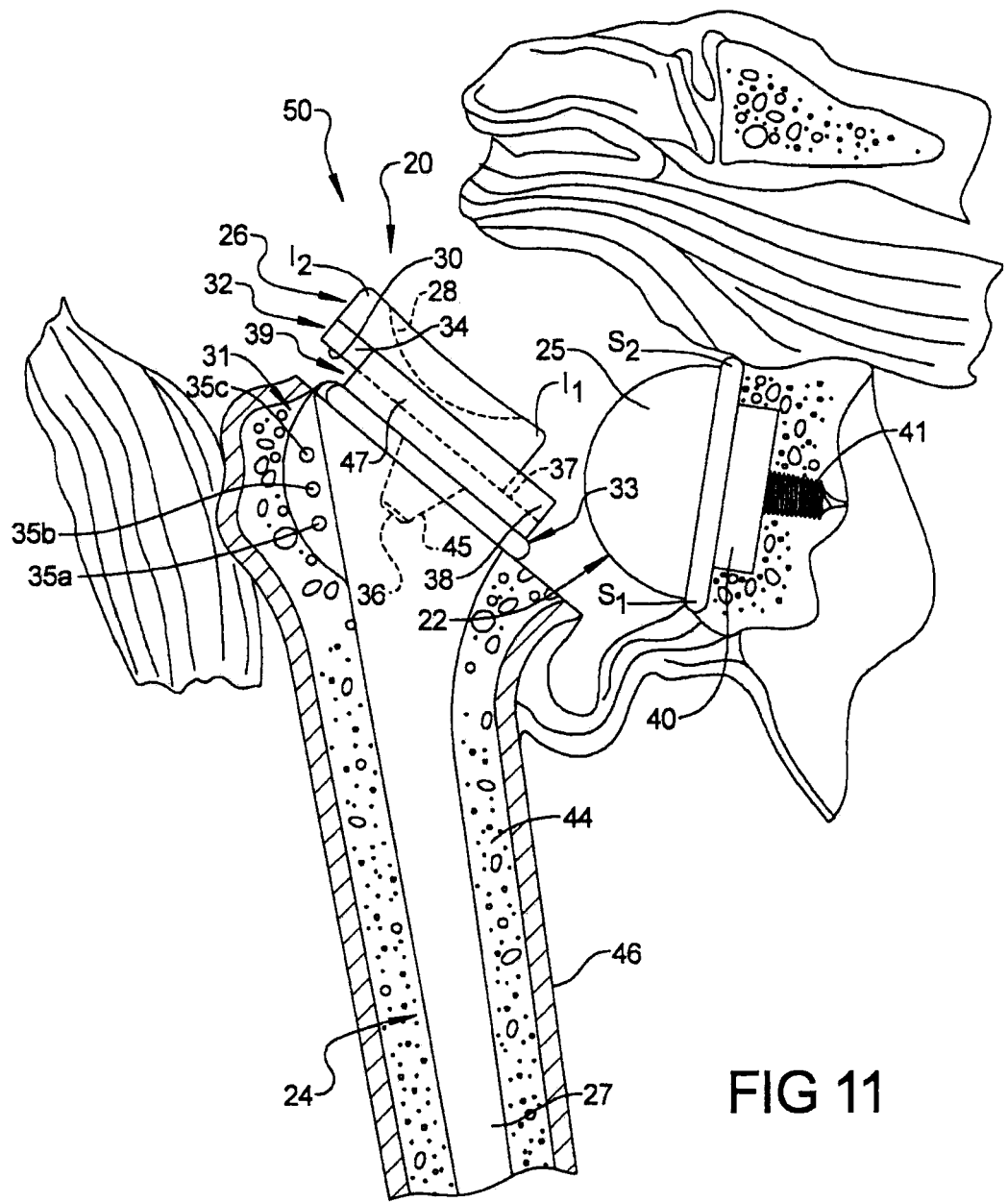
FIG. 11 depicts the insertion of the humeral implant shown in FIG. 1.

FIG. 1 represents an exploded view of a shoulder implant 20 according to the present teachings. The shoulder implant 20 can include a fixed bearing 22, a stem 24 and a floating bearing 26. The fixed bearing 22 can be fixably coupled to a prepared glenoid (FIG. 11). The fixed bearing 22 can have an articulating surface 25 and a coupling mechanism 23 configured to couple the fixed bearing 22 to a prepared glenoid. In one example, the articulating surface 25 can comprise a convex articulating surface, but it should be noted that the articulating surface 25 could be concave. In addition, it should be noted that the articulating surface 25 can have any desired shape, such as hemispherical, spherical, etc. to articulate with the floating bearing 26. With brief reference to FIG. 11, the fixed bearing 22 can be coupled to a prepared glenoid using an intermediate member, such as a base member 40, which can be coupled to the prepared glenoid using a fastener such as a bone fastener 41, as will be discussed in greater detail herein. With reference back to FIG. 1, the fixed bearing 22 can also include at least one stop surface, such as a stop surface $S_1$ and stop surface $S_2$. The stop surface $S_1$ and stop surface $S_2$ can be formed generally about a circumference of the fixed bearing 22, however, the stop surface $S_1$ and stop surface $S_2$ can have any desired shape. The stop surface $S_1$ and stop surface $S_2$ can cooperate with the floating bearing 26 to cause the floating bearing 26 to move relative to the fixed bearing 22, as will be discussed in greater detail herein. The fixed bearing 22 can be composed of a suitable biocompatible material, such as a biocompatible metal or polymer, and in one example, the fixed bearing 22 can be composed of a polymer.

With reference to FIG. 1, the stem 24 can be positioned within a prepared intramedullary canal in an anatomy, such as a humerus. The stem 24 can be composed of a suitable biocompatible material, such as a metal or a polymer. In one example, the stem 24 can be composed of a titanium alloy or cobalt chromium molybdenum alloy. The stem 24 can also be coated with bioabsorbable material, such as polylactides, polyglycolides, calcium phosphate, hydroxyapatite, etc. The stem 24 can be generally elongated, and can include a first end 27 and a second end 29. The first end 27 can be tapered to be received within the prepared canal of the humerus. The second end 29 can include a flange 31 and a coupling surface 33. The flange 31 can project outwardly from the second end 29 and can include at least one aperture 35. In one example, the at least one aperture 35 can comprise three apertures 35a-35c. The apertures 35a-35c can receive a fastening device, such as a suture, to further assist in securing the stem 24 to the anatomy.

With reference to FIG. 2, the coupling surface 33 can be substantially smooth and planar. The coupling surface 33 can also define a bore 36. The bore 36 can be defined generally at a center of the coupling surface 33. As will be discussed, the bore 36 can receive a portion of an intermediate coupling member 39 to couple the intermediate coupling member 39 to the stem 24. If desired, the bore 36 can include a taper, which can mate or lock with the portion of the intermediate coupling member 39.

With reference to FIG. 1, the floating bearing 26 can have a pair of articulating bearing surfaces 28 and 30. The first bearing surface 28 can be a generally spherical articulating surface configured to articulate with the convex articulating surface 25 of the fixed bearing 22 (FIG. 2). It should be noted that the first bearing surface 28 can be concave or convex. The first bearing surface 28 can be curved along substantially its entire length and can be flush with the articulating surface 25 when stop surface $S_1$ or stop surface $S_2$ of the fixed bearing 22 is engaged with the floating bearing 26.

Figure 6A:
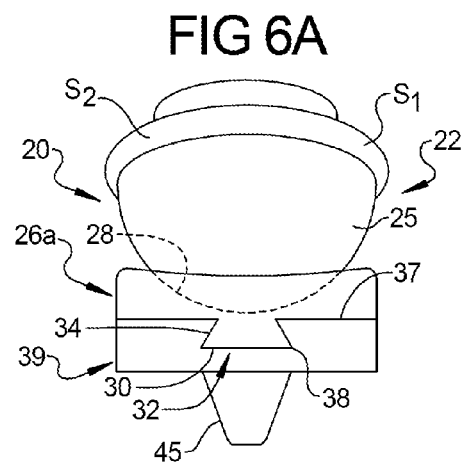
FIGS. 6A and 6B are end views of a humeral implant according to the present teachings.

With continued reference to FIG. 1, the second bearing surface 30 can comprise a generally planar polished surface configured to allow linear translation of the floating bearing 26 with respect to stem 24. The floating bearing 26 can be coupled to the stem 24 via a coupling mechanism 32 disposed on the planar second bearing surface 30. In one example, the coupling mechanism 32 can define a coupling portion 34, which can engage a slot 38 of an intermediate coupling member 39 as will be discussed in further detail herein. In one example, as illustrated in FIG. 6A, the coupling portion 34 and slot 38 can cooperate as a dovetail coupling mechanism. It should be noted that the use of a dovetail coupling mechanism is merely exemplary as any suitable coupling mechanism could be employed to enable the floating bearing 26 to move relative to the stem 24, such as a T-shaped rail configuration, etc. The coupling mechanism 32 can constrain movement of the floating bearing 26, but can allow linear translation of the floating bearing 26 with respect to the stem 24. The linear translation can be along a line which intersects an axis of the bore 36 of the stem 24. It is envisioned that secondary stops in the form of a pin in a slot disposed between the second bearing surface 30 and the planar bearing surface 37 can be used to limit the travel of the floating bearing 26 with respect to the stem 24.

Figure 6B:
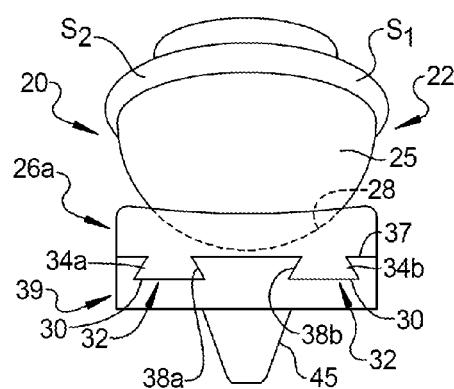
Figure 7:
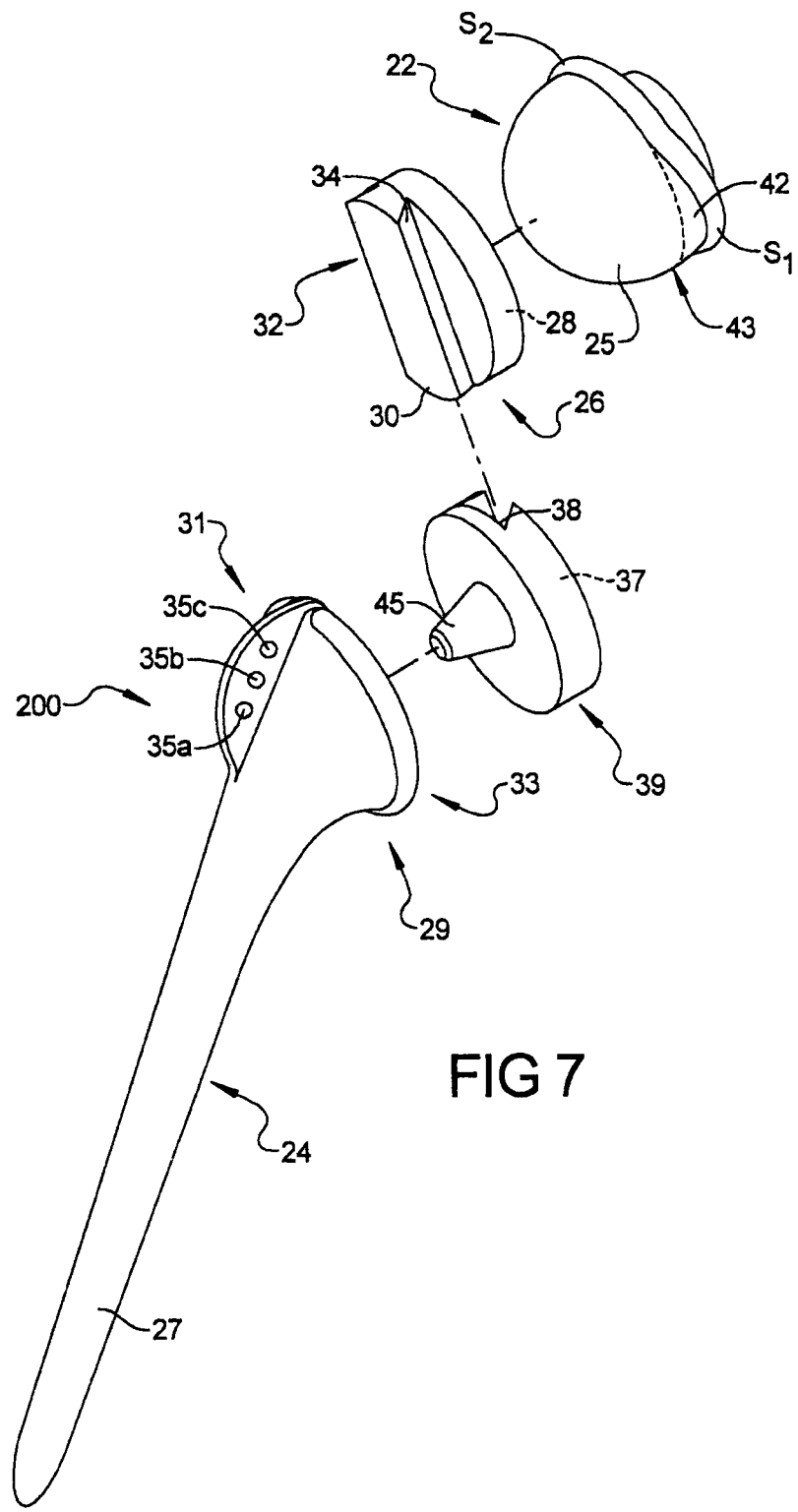
FIG. 7 is an exploded view of an alternate humeral implant according to the present teachings.
Figure 8:
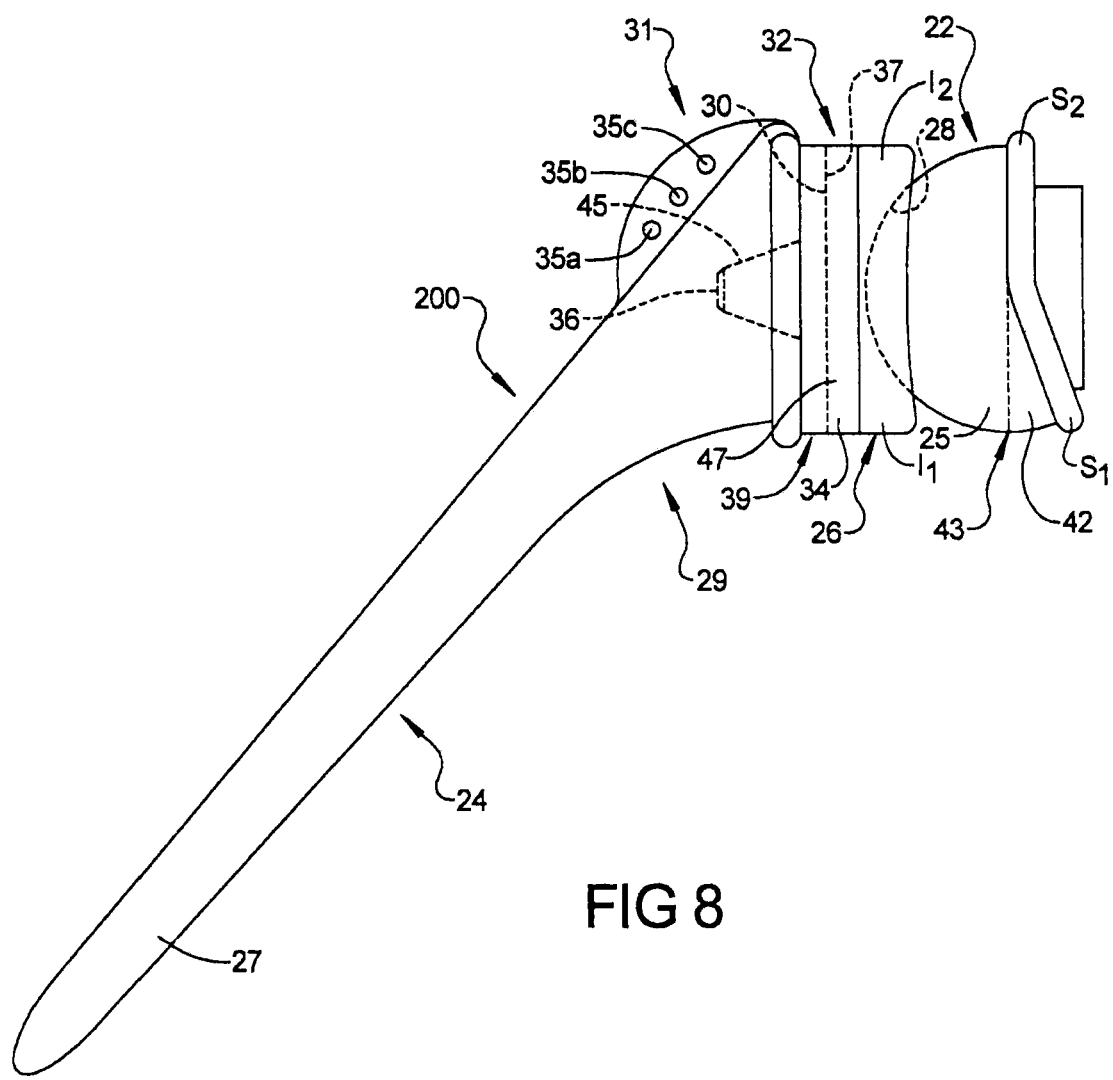
FIG. 8 is an assembled view of a humeral implant according to the teachings of FIG. 7 in a first position.

In addition, it is envisioned the coupling mechanism 32 can take the form of single or multiple flanges which interface with a slot or slots formed within the floating bearing 26. In this regard, in an alternate embodiment, with reference to FIG. 6B, a floating bearing 26a can move relative to the stem 24 via two coupling mechanisms 32. In this example, each of the coupling mechanisms 32 can include coupling portions 34a, 34b, which can movably engage substantially parallel slots 38a, 38b formed in the intermediate coupling member 39. It should be noted that the use of two substantially parallel coupling mechanisms 32 is merely exemplary as any number of coupling mechanisms 32 could be used in any desired orientation.

With reference back to FIG. 1, the intermediate coupling member 39 can be disposed between the floating bearing 26 and the stem 24. The intermediate coupling member 39 can include a body portion 47 defining the slot 38, which can comprise a planar bearing surface 37. The planar bearing surface 37 can be configured to slidably interface with the planar second bearing surface 30. The engagement between the slot 38 and coupling portion 34 of the floating bearing 26 can enable the floating bearing 26 to move relative to the stem 24. The intermediate coupling member 39 can also include a coupling portion 45 for coupling the intermediate coupling portion 45 to the bore 36 of the stem 24. In one example, the coupling portion 45 can comprise a tapered portion, which can engage a mating taper formed in the bore 36 to couple the intermediate coupling member 39 to the stem 24. It should be noted, however, that any suitable technique can be used to couple the intermediate coupling member 39 to the stem 24, such as a mechanical fastener, welding, etc. The intermediate coupling member 39 can be comprised of any suitable biocompatible material, such as a biocompatible metal or polymer. In one example, the intermediate coupling member 39 can be comprised of a titanium alloy or a cobalt chromium molybdenum alloy. In addition, the intermediate coupling member 39 can be coated with a bioabsorbable material, such as polylactides, polyglycolides, calcium phosphate, hydroxyapatite, etc.

As shown in FIG. 2, in its implanted position, the floating bearing 26 can be coupled to the stem 24 using the intermediate coupling member 39. In the absence of forces on the stem 24, the floating bearing 26 can be generally centered with respect to the intermediate coupling member 39. The stem 24 can be configured to rotate about the fixed bearing 22 between a first angular location $A_1$, and a second angular location $A_2$.

As shown in FIGS. 3A-3C, a location of first and second interface surfaces $I_1$ and $I_2$ can be varied with respect to the second bearing surface 30, thus adjusting the first angular location $A_1$ and second angular location $A_2$. The first interface surface $I_1$ can be a first distance from the planar second bearing surface 30, while the second interface surface $I_2$ can be a second distance from the second bearing surface 30, the second distance optionally being different or greater than the first distance. The first and second interface surfaces $I_1$ and $I_2$ can cooperate with the stop surfaces $S_1$ and $S_2$ to control the motion of the shoulder implant 20. A kit of floating bearings 26 can be provided to allow the treating physician to vary the amount of articulation of the stem 24 before the interface surfaces $I_1$ and $I_2$ contact the stop surfaces $S_1$ and $S_2$ located on the fixed bearing 22. Although not shown, it is envisioned that the location or size of the stop surfaces $S_1$ and $S_2$ on the fixed bearing 22 can be adjusted with respect to the coupling mechanism 32 to adjust the dynamics of the shoulder implant 20.

Figure 4:
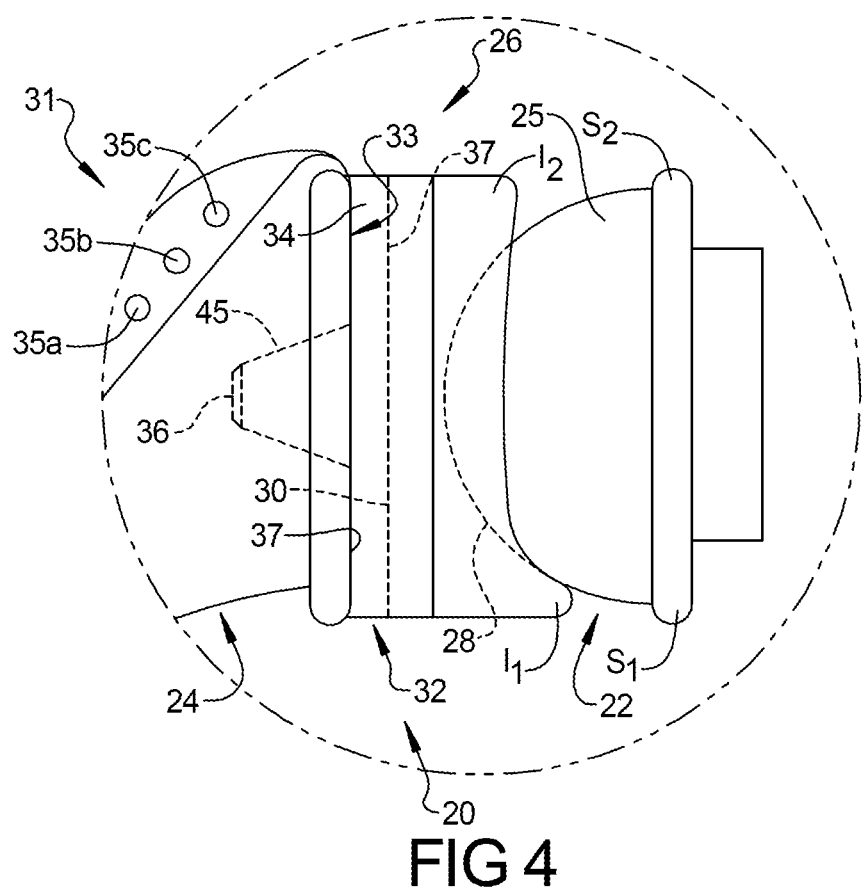
FIG. 4 is a side assembled environmental view of a humeral implant using the floating bearing shown in FIG. 3A according to the present teachings.

FIG. 4 represents a close up view of the stop surfaces $S_1$ and $S_2$ of the fixed bearing 22 and the first and second interface surfaces $I_1$ and $I_2$ of the floating bearing 26. The stop surfaces $S_1$ and $S_2$ can have a shape which, when engaged with the floating bearing 26, can apply a force to a respective one of the first and second interface surfaces $I_1$ and $I_2$ of the floating bearing 26. The application of force by the stop surfaces $S_1$ and $S_2$ onto the respective first and second interface surfaces $I_1$ and $I_2$ can cause movement or translation of the floating bearing 26 relative to the fixed bearing 22.

Figure 5:
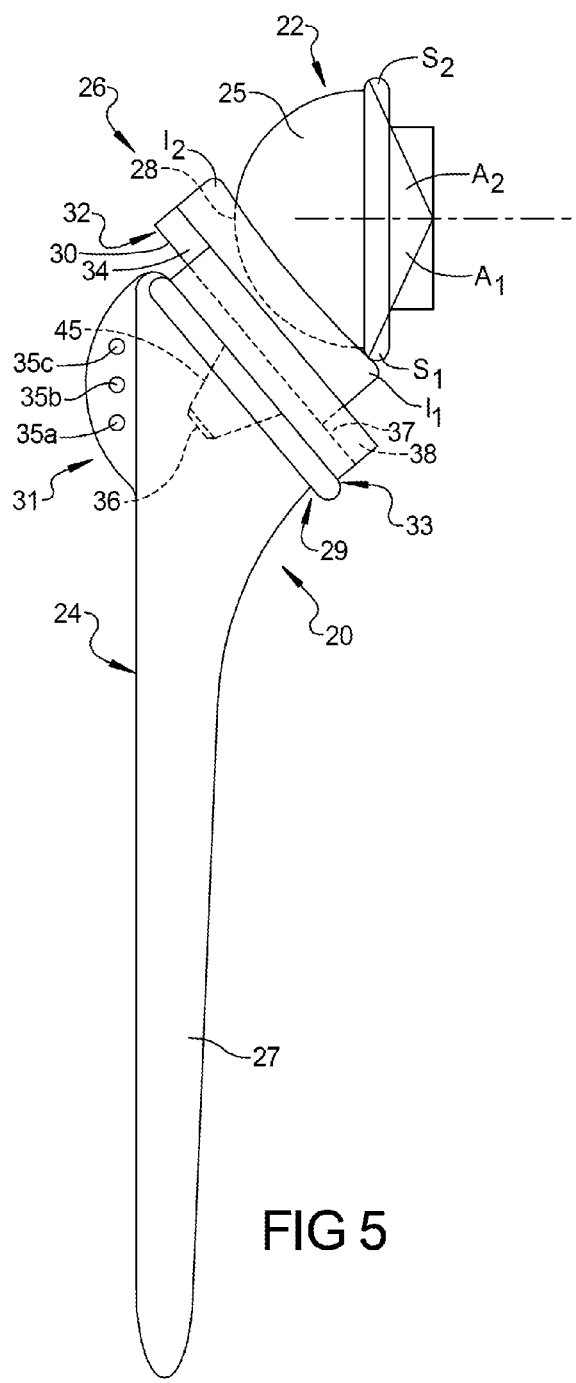
FIG. 5 is an assembled view of a humeral implant according to the present teachings in a first position.

As best seen in FIG. 5, rotation of the stem 24 to the first angular location $A_1$ can allow the engagement of the first interface surface $I_1$ with the stop surface $S_1$ located on the articulating surface 25 of the fixed bearing 22. The stop surface $S_1$ can apply force onto the floating bearing 26, thus translating the floating bearing 26 from a first position to a second position with respect to the stem 24. This can displace the stem 24 with respect to the fixed bearing 22, thereby allowing for a greater range of motion for the shoulder joint.

FIGS. 7, 8, 9A-9B and 10B represent a shoulder implant 200 according to the present teachings that utilizes a fixed bearing 22 having an extended articulating surface 42. The extended articulating surface 42 can allow further rotation of the stem 24 past an equatorial line 43 on the fixed bearing 22. The stop surface $S_1$ can be positioned to allow translation to the first angular location $A_1$ (see FIG. 9A) at which point the stop surface $S_1$ can engage the floating bearing 26. Optionally, the stop surface $S_1$ can be formed as a pair of flanges extending from the floating bearing 26 or the fixed bearing 22.

Figures 9A, 9B:
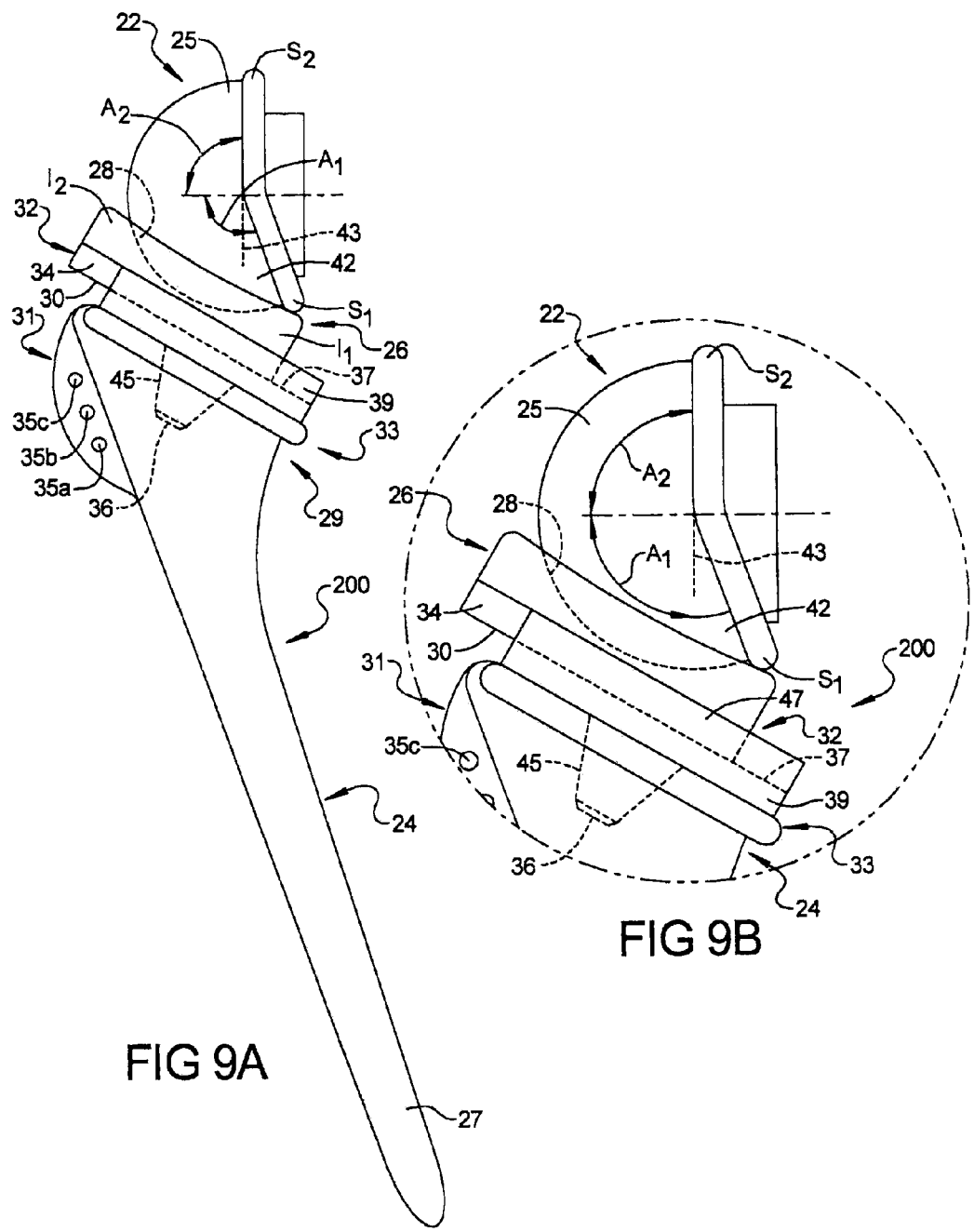
FIGS. 9A and 9B are assembled views of a humeral implant according to the present teachings in a second position.

In a medial position, movement of the stem 24 allows for normal rotation of the floating bearing 26 with respect to the fixed bearing 22. Further rotation of the stem 24 causes the stop surface $S_1$ to engage the first interface surface $I_1$ of the floating bearing 26. This interaction applies pressure onto the floating bearing 26, thus allowing translation of the stem 24 with respect to the fixed bearing 22. Referring briefly to FIGS. 9A and 9B, in this example, the first and second angular locations $A_1$ and $A_2$ can be defined by interactions between the stop surfaces $S_1$ and $S_2$ and first and second interface surfaces $I_1$ and $I_2$ located on the floating bearing 26. The first and second angular locations $A_1$ and $A_2$ can be adjusted by adjusting the positions of the stop surfaces $S_1$ and $S_2$ and the positions of the first and second interface surfaces of $I_1$ and $I_2$.

Figure 10A:
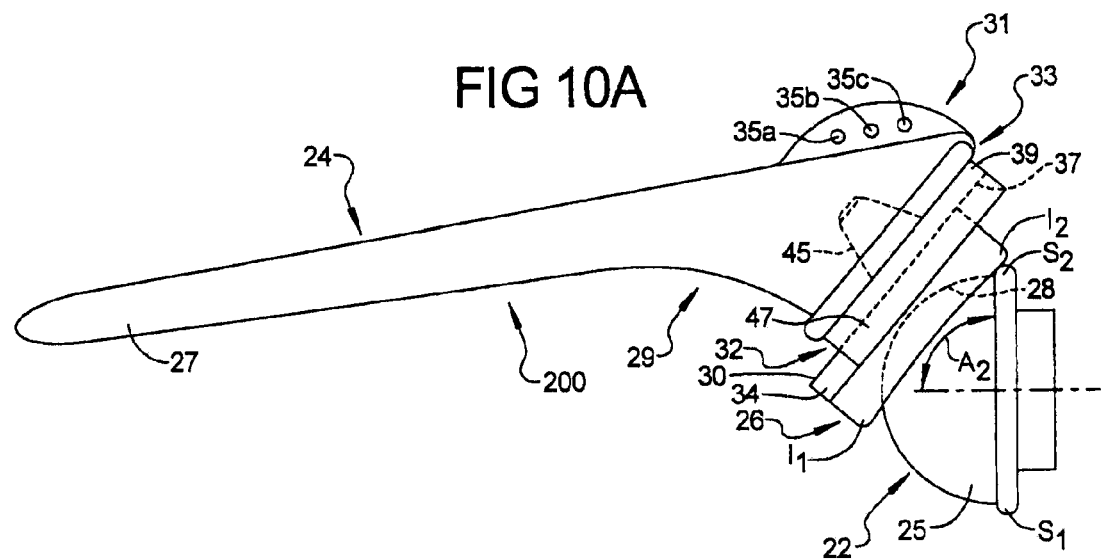
FIGS. 10A and 10B represent the implants of FIGS. 1 and 7 in a third position.
Figure 10B:
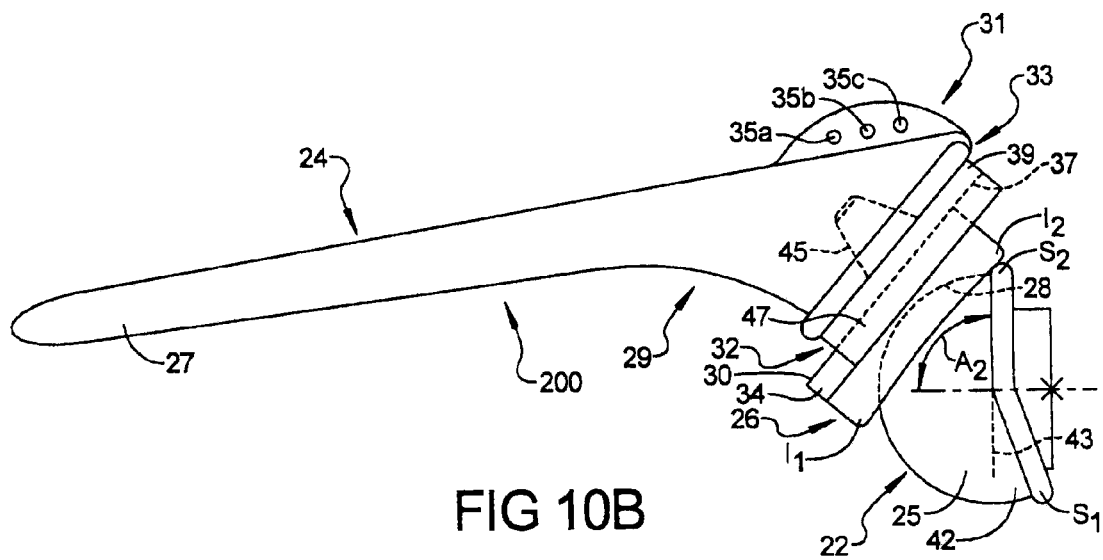

As shown in FIGS. 10A and 10B, the rotation of the stem 24 to the second angular location $A_2$ causes an interaction of the stop surface $S_2$ with the second interface surface $I_2$. Forces applied to the stem 24 by the anatomy can pull the stem 24 in a medial direction, thus allowing increased rotational movement of the shoulder joint. As previously described, adjustment of the first and second interface surfaces $I_1$ and $I_2$ with respect to the first and second stop surfaces $S_1$ and $S_2$ can be used to change joint dynamics.

With reference to FIG. 11, FIG. 11 depicts the coupling of the shoulder implant 20 with a prepared humeral/glenoid joint. It should be noted that the shoulder implant 200 can be coupled to the humeral/glenoid joint in a manner substantially similar to the shoulder implant 20 and thus, the coupling of the shoulder implant 200 to the anatomy is not illustrated herein. Prior to insertion of the glenospherical fixed bearing 22, a glenoid can be reamed to prepare a flat surface. The base member 40 can then be coupled to the prepared glenoid using the bone fastener 41. In one example, the fixed bearing 22 including the stop surfaces $S_1$ and $S_2$ can then be coupled to the base member 40. Optionally, the base member 40 can define the stop surfaces $S_1$ and $S_2$.

Next, the humerus 46 can be prepared by resecting the humeral head and preparing the medullary canal 44. The stem 24 can then be coupled to the humerus using known technologies. It is envisioned that this exemplary surgical procedure can be accomplished through a single incision 50.

With the stem 24 coupled to the humerus, the intermediate coupling member 39 can be coupled to the stem 24 via the coupling portion 45. Optionally, the intermediate coupling member 39 can be fixed to the stem 24 using any suitable coupling technique, such as a mechanical fastener, welding, etc. In the example of a kit of floating bearings 26, trial floating bearings 26 can be used to determine an ideal floating bearing 26 for use with the anatomy. In one example, this can be accomplished by testing the range of motion of the shoulder joint. Based upon this determination, a proper floating bearing 26 can be coupled to the base member 40 by sliding the coupling portion 34 into the slot 38 using a cross-axis sliding engagement.

Thus, the floating bearing 26 can provide a greater range of motion for the shoulder implant 20. The interaction between the stop surfaces $S_1$ and $S_2$ of the fixed bearing 22 and the first and second interface surfaces $I_1$ and $I_2$ of the floating bearing 26 can allow for increased rotational movement of the shoulder joint without coming into contact with the scapula.

While specific examples have been described in the specification and illustrated in the drawings, it will be understood by those of ordinary skill in the art that various changes can be made and equivalents can be substituted for elements thereof without departing from the scope of the present teachings. Furthermore, the mixing and matching of features, elements and/or functions between various examples is expressly contemplated herein so that one of ordinary skill in the art would appreciate from the present teachings that features, elements and/or functions of one example can be incorporated into another example as appropriate, unless described otherwise, above. Moreover, many modifications can be made to adapt a particular situation or material to the present teachings without departing from the essential scope thereof. Therefore, it is intended that the present teachings not be limited to the particular examples illustrated by the drawings and described in the specification, but that the scope of the present teachings will include any embodiments falling within the foregoing description.

What is claimed is:

1. A shoulder implant comprising:
 a fixed bearing defining a stop surface and having a generally spherical articulating surface configured to be coupled to a glenoid;
 a floating bearing member defining a first spherical bearing surface and a second planar articulating bearing surface, wherein the first spherical bearing surface cooperates with the generally spherical articulating surface of the fixed bearing; and
 a stem defining a stem planar bearing surface coupled to the second planar articulating bearing surface, wherein the second planar articulating bearing surface cooperates with the stem planar bearing surface to enable the floating bearing to translate relative to the stem when the floating bearing member is contacted by the stop surface.

2. The shoulder implant according to claim 1, wherein the stop surface is configured to apply a force to the floating bearing member when the stem is in a first position.

3. The shoulder implant according to claim 2, wherein the force causes the floating bearing member to translate relative to the stem.

4. The shoulder implant according to claim 2, wherein the stem translates in a first direction when the stop surface applies the force on a first surface of the floating bearing member.

5. The shoulder implant according to claim 4, wherein the stem translates in a second direction when the stop surface applies the force to a second surface of the floating bearing member.

6. The shoulder implant according to claim 4, wherein the stop surface comprises two flange portions disposed at opposing ends of the fixed bearing member.

7. The shoulder implant according to claim 1, wherein the floating bearing member defines a first interface surface a first distance from the second planar articulating surface, the first interface surface configured to interface with the stop surface.

8. The shoulder implant according to claim 7, wherein the floating bearing member defines a second interface surface a second distance from the second planar articulating surface, the second distance being greater than the first distance, the second interface surface configured to interface with the stop surface.

9. The shoulder implant according to claim 1, wherein the floating bearing member defines first and second interface surfaces configured to interface with the stop surface and restrict relative rotation there between.

10. The shoulder implant according to claim 1, wherein the fixed bearing has an extended articulating surface.

11. A shoulder implant comprising:
 a fixed bearing having a spherical articulating surface;
 a floating bearing having a first surface that articulates with the fixed bearing spherical articulating surface, the floating bearing defining a translatable planar bearing having a second planar articulating surface; and
 a stem having a planar bearing surface that engages and translates the translatable second planar articulating surface,
 wherein the fixed bearing comprises a stop surface operably positioned to limit movement of the fixed bearing with respect to the stem when the fixed bearing articulates with the floating bearing.

12. The shoulder implant according to claim 11, wherein the stop surface is a flange.

13. The shoulder implant according to claim 11, wherein the floating bearing defines a first interface surface a first distance from the second planar articulating surface, the first interface surface configured to interface with the stop surface.

* * * * *